(12) United States Patent
Coillard-Lavirotte et al.

(10) Patent No.: US 10,292,746 B2
(45) Date of Patent: May 21, 2019

(54) SURGICAL TOOL HAVING A CANNULA, A SURGICAL KIT, A METHOD OF FABRICATION, AND A MACHINE FOR FABRICATING SUCH A TOOL

(71) Applicant: IN2BONES, Ecully (FR)

(72) Inventors: Jean-Yves Paul Albert Coillard-Lavirotte, Saint Cyr au Mont d'or (FR); Daniel Edmond Boublil, Lyons (FR); Philippe Emmanuel D'Ingrado, Saint Didier au Mont'Dor (FR)

(73) Assignee: IN2BONES, Ecully (FR)

( * ) Notice: Subject to any disclaimer, the term of this patent is extended or adjusted under 35 U.S.C. 154(b) by 555 days.

(21) Appl. No.: 14/824,301

(22) Filed: Aug. 12, 2015

(65) Prior Publication Data
US 2016/0045239 A1    Feb. 18, 2016

(30) Foreign Application Priority Data

Aug. 13, 2014 (FR) ...................................... 14 57782

(51) Int. Cl.
*A61B 17/88* (2006.01)
*A61B 17/34* (2006.01)
(Continued)

(52) U.S. Cl.
CPC .......... *A61B 17/88* (2013.01); *A61B 17/3421* (2013.01); *A61B 17/8872* (2013.01);
(Continued)

(58) Field of Classification Search
CPC . A61B 17/88; A61B 17/8875; A61B 17/8877; A61B 17/888; A61B 17/8886; A61B 17/8888
See application file for complete search history.

(56) References Cited

U.S. PATENT DOCUMENTS 6,398,785 B2 * 6/2002 Carchidi ............ A61B 17/8615
606/312
9,131,946 B2 * 9/2015 Larche ................. A61B 17/888
(Continued)

FOREIGN PATENT DOCUMENTS

DE 102012104973 A1 3/2013
FR 2739016 A1 3/1997

OTHER PUBLICATIONS

International Search Report for FR1457782.

*Primary Examiner* — Eric S Gibson
(74) *Attorney, Agent, or Firm* — McClure, Qualey & Rodack, LLP

(57) ABSTRACT

The invention provides a surgical tool (1), e.g. a hand-held tool, for inserting surgical implants in a patient's body, the tool comprising:
  a main body (2) extending along a longitudinal axis (X-X') between firstly a working end (3) and secondly a proximal end (4), the main body (2) also presenting an outside surface (5) connecting the working end (3) to the proximal end (4); and
  a guide cannula (14) arranged within the main body (2) and extending between a distal orifice (15) opening to the outside of said main body (2) at the working end (3), and a rear orifice (16);
said surgical tool (1) being characterized in that said rear orifice (16) opens out to the outside surface (5) of said main body (2), and in that said main body (2) presents longitudinal splines (25, 27, 28) projecting from said main body (2) in respective planes extending. radially relative to the longitudinal axis (X-X').
Surgical instrumentation.

21 Claims, 2 Drawing Sheets

(51) Int. Cl.
  *B29C 39/10* (2006.01)
  *B29C 45/14* (2006.01)
  *A61B 17/56* (2006.01)
  *B29L 31/00* (2006.01)
  *A61F 2/46* (2006.01)

(52) U.S. Cl.
  CPC .......... *A61B 17/8875* (2013.01); *B29C 39/10* (2013.01); *B29C 45/14467* (2013.01); *A61B 17/8897* (2013.01); *A61B 2017/564* (2013.01); *A61F 2002/4677* (2013.01); *B29L 2031/7548* (2013.01)

(56) References Cited

U.S. PATENT DOCUMENTS

| | | | | |
|---|---|---|---|---|
| 9,572,605 | B2* | 2/2017 | Shipp | A61B 17/7082 |
| 9,775,702 | B2* | 10/2017 | Arai | A61B 17/0401 |
| 9,840,002 | B2* | 12/2017 | Schon | B25B 15/008 |
| 9,949,820 | B2* | 4/2018 | Housman | A61B 17/0401 |
| 9,968,384 | B2* | 5/2018 | Fischer | A61B 17/708 |
| 2001/0004694 | A1* | 6/2001 | Carchidi | A61B 17/8615 606/312 |
| 2001/0004710 | A1 | 6/2001 | Felt et al. | |
| 2001/0022120 | A1* | 9/2001 | Mark | A61B 17/888 81/452 |
| 2004/0255734 | A1* | 12/2004 | Casutt | A61B 17/8875 81/467 |
| 2005/0216015 | A1* | 9/2005 | Kreidler | A61B 17/8605 606/916 |
| 2005/0222575 | A1* | 10/2005 | Ciccone | A61B 17/1615 606/104 |
| 2007/0005077 | A1* | 1/2007 | Null | A61B 17/862 606/104 |
| 2011/0245881 | A1* | 10/2011 | Mitchell | A61B 17/7098 606/304 |
| 2011/0301614 | A1* | 12/2011 | Impellizzeri | A61B 17/8615 606/104 |
| 2012/0059384 | A1* | 3/2012 | Fan | A61F 2/0805 606/104 |
| 2012/0179163 | A1* | 7/2012 | Housman | A61B 17/0401 606/104 |
| 2013/0096568 | A1* | 4/2013 | Justis | A61B 17/8875 606/104 |
| 2013/0150864 | A1* | 6/2013 | Marik | A61B 17/8888 606/104 |
| 2013/0178901 | A1* | 7/2013 | Arai | A61B 17/0401 606/233 |
| 2013/0226239 | A1* | 8/2013 | Altarac | A61B 17/7064 606/247 |
| 2013/0282019 | A1* | 10/2013 | Bouliane | A61B 17/7082 606/104 |
| 2013/0304068 | A1* | 11/2013 | Larche | A61B 17/888 606/79 |
| 2014/0100616 | A1* | 4/2014 | Shipp | A61B 17/7082 606/86 A |
| 2014/0207233 | A1* | 7/2014 | Steiner | A61B 17/8875 623/13.14 |
| 2014/0257408 | A1* | 9/2014 | Trieu | A61B 17/8875 606/301 |
| 2015/0032116 | A1* | 1/2015 | Jerke | A61B 17/8875 606/104 |
| 2015/0196340 | A1* | 7/2015 | Combrowski | A61B 17/8875 606/102 |
| 2015/0201986 | A1* | 7/2015 | Stank | A61B 17/8875 606/104 |
| 2015/0282855 | A1* | 10/2015 | Bess | A61B 17/8875 606/86 A |
| 2016/0045239 | A1* | 2/2016 | Coillard-Lavirotte | A61B 17/88 606/86 R |
| 2017/0224399 | A1* | 8/2017 | Coillard-Lavirotte | A61B 17/8875 |
| 2018/0214190 | A1* | 8/2018 | Erramilli | A61B 17/7082 |

* cited by examiner

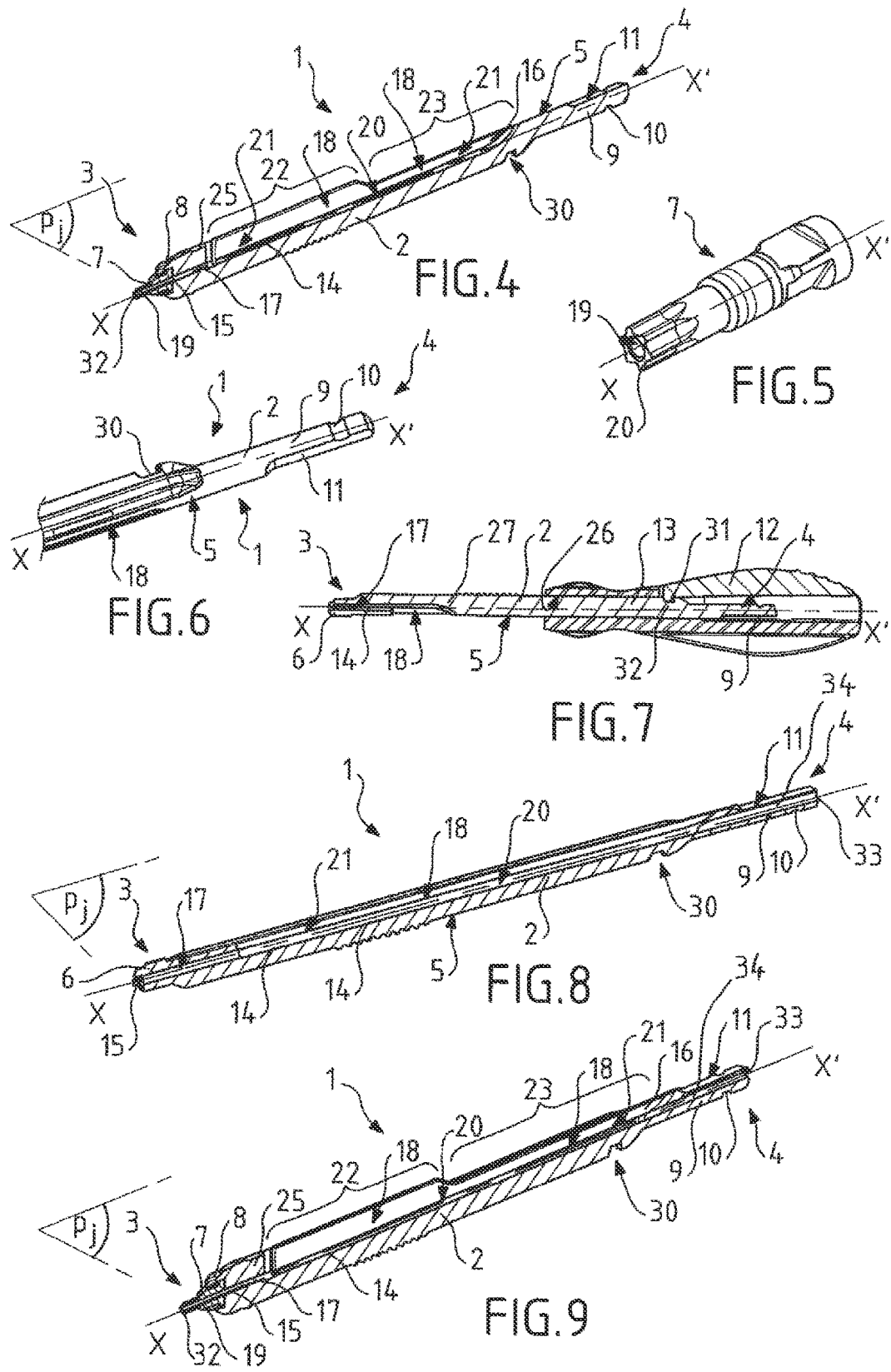

SURGICAL TOOL HAVING A CANNULA, A SURGICAL KIT, A METHOD OF FABRICATION, AND A MACHINE FOR FABRICATING SUCH A TOOL

CROSS REFERENCE RELATED APPLICATIONS

This application claims priority to French Application Serial No. 1457782 filed Aug. 13, 2014, which is entirely incorporated herein by reference.

The present invention relates to the field of surgical instruments, in particular surgical tools having cannulas, such as a surgical screwdriver with a cannula, the cannula being for receiving, for example, a wire for putting osteosynthesis implants into place.

The invention provides in particular to a surgical tool, e.g. a hand-held tool, for inserting surgical implants in a patient's body, the tool comprising:
  a main body extending along a longitudinal axis between firstly a working end and secondly a proximal end, the main body also presenting an outside surface connecting the working end to the proximal end; and
  a guide cannula arranged within the main body and extending between a distal orifice opening to the outside of said main body at the working end, and a rear orifice.

The invention also provides a surgical kit comprising at least one surgical tool.

The invention also provides a method of fabricating a surgical tool.

Finally, the invention provides a machine for fabricating a surgical tool.

In the field of surgical instrumentation for implanting osteosynthesis implants in a patient's body, screwdriver-type tools are known that present a cannula extending from the distal end of the tool to its proximal end. The main function of the cannula is to enable the tool to be guided with the help of a guide wire previously implanted in the patient's bone, with the surgeon being able to engage the tool on the guide wire in order to slide the tool along said guide wire. This makes it possible to implant an implant in the patient's body, such as an osteosynthesis screw, in a manner that is relatively accurate and reliable.

Guide wires are usually in the form of a relatively long rectilinear metal rod and it is necessary to provide a cannula of length that is longer than the length of the wire in order to be able to insert the wire fully within the tool. Tools of length that is shorter than the length of the guide wire generally have the cannula passing right through them.

Nevertheless, making a cannula of long length can be difficult. In particular, it is generally necessary to fabricate the tool with a cannula in at least two steps.

For example, such a tool may be fabricated using a first step of making a tool without a cannula, followed by a step of drilling the tool without a cannula in the longitudinal direction in order to form the cannula. The drilling step can require great accuracy, in particular in order to guarantee that the hole is true, especially when the hole is long relative to its diameter, so that fabrication of the tool turns out to be lengthy and expensive.

Furthermore, in certain circumstances, the quality of the resulting cannula can be found to be inadequate: specifically, it is possible for the diameter of said cannula not to be constant all along the cannula, such that the guidance of known the surgical tool provided by the wire can be found to be inadequate and uncertain. Furthermore, the sliding of the wire within the cannula may possibly be braked by imperfections in the shape of the inside of the cannula. Finally, under certain circumstances, creating a cannula by drilling can weaken the general structure of the surgical tool, and make it brittle, which might endanger the surgical operation being performed on the patient.

Consequently, the objects assigned to the present invention seek to remedy the various drawbacks listed above and to propose a novel surgical tool, a novel surgical kit, a novel method of fabrication, and a novel fabrication machine, making it possible to reduce fabrication time and the cost of surgical tools with cannulas.

Another object of the invention seeks to provide a novel surgical tool, a novel surgical kit, a novel method of fabrication, and a novel fabrication machine making it possible to facilitate the fabrication of surgical tools with cannulas.

Another object of the invention seeks to provide a novel surgical tool, a novel surgical kit, a novel method of fabrication, and a novel fabrication machine making it possible to design and fabricate surgical tools with cannulas that are particularly robust and reliable.

Another object of the invention seeks to provide a novel surgical tool, a novel surgical kit, a novel method of fabrication, and a novel fabrication machine making it possible to design and fabricate surgical tools with cannulas that are disposable or for single use.

Another object of the invention seeks to provide a novel surgical tool, a novel surgical kit, a novel method of fabrication, and a novel fabrication machine making it possible to improve and facilitate cleaning the surgical environment.

Another object of the invention seeks to provide a novel surgical tool, a novel surgical kit, a novel method of fabrication, and a novel fabrication machine making it possible to obtain particularly high accuracy in the surgical procedure.

Another object of the invention seeks to provide a novel surgical tool, a novel surgical kit, a novel method of fabrication, and a novel fabrication machine making it possible to design surgical tools in which the cannula can receive a guide wire that is particularly long.

Another object of the invention seeks to provide a novel surgical tool, a novel surgical kit, a novel method of fabrication, and a novel fabrication machine making it possible to design surgical tools with cannulas that are particularly versatile.

The objects given to the invention are achieved with the help of a surgical tool, e.g. a hand-held tool, for inserting surgical implants in a patient's body, the tool comprising:
  a main body extending along a longitudinal axis between firstly a working end and secondly a proximal end, the main body also presenting an outside surface connecting the working end to the proximal end; and
  a guide cannula arranged within the main body and extending between a distal orifice opening to the outside of said main body at the working end, and a rear orifice;
  said surgical tool being characterized in that said rear orifice opens out to the outside surface of said main body, and in that said main body presents longitudinal splines projecting from said main body in respective planes extending radially relative to the longitudinal axis X-X'.

The objects assigned to the invention are also achieved with the help of a surgical kit comprising at least one surgical tool of the invention together with a removable handle.

The objects assigned to the invention are also achieved with the help of a fabrication method for fabricating a surgical tool of the invention, characterized in that it comprises a single molding step during which said surgical tool is made in full.

Finally, the objects assigned to the invention are achieved using a machine for fabricating a surgical tool that enables the fabrication method of the invention to be performed.

Other features and advantages of the invention appear and are revealed in greater detail on reading the following description made with reference to the accompanying drawings, given purely by way of non-limiting illustrative example, and in which:

FIG. 4 is a longitudinal section view in perspective showing an embodiment detail of the second variant of the FIG. 3 surgical tool;

FIG. 5 is a perspective view showing the fitted working endpiece of FIGS. 3 and 4;

FIG. 6 is a perspective view showing an embodiment detail that is common to the first and second variants of the surgical tool shown in FIGS. 1 to 4;

FIG. 7 is a side view in section showing the first variant surgical tool combined with a removable handle so as to co-operate therewith to form a surgical instrument with a removable handle;

FIG. 8 is a longitudinal section view in perspective showing a third variant of a surgical tool in accordance with the invention, including in particular an extension working endpiece, and a proximal orifice; and FIG. 9 is a longitudinal section view in perspective showing a fourth variant of a surgical tool in accordance with the invention, including in particular a fitted working endpiece and a proximal orifice.

Figure 1:
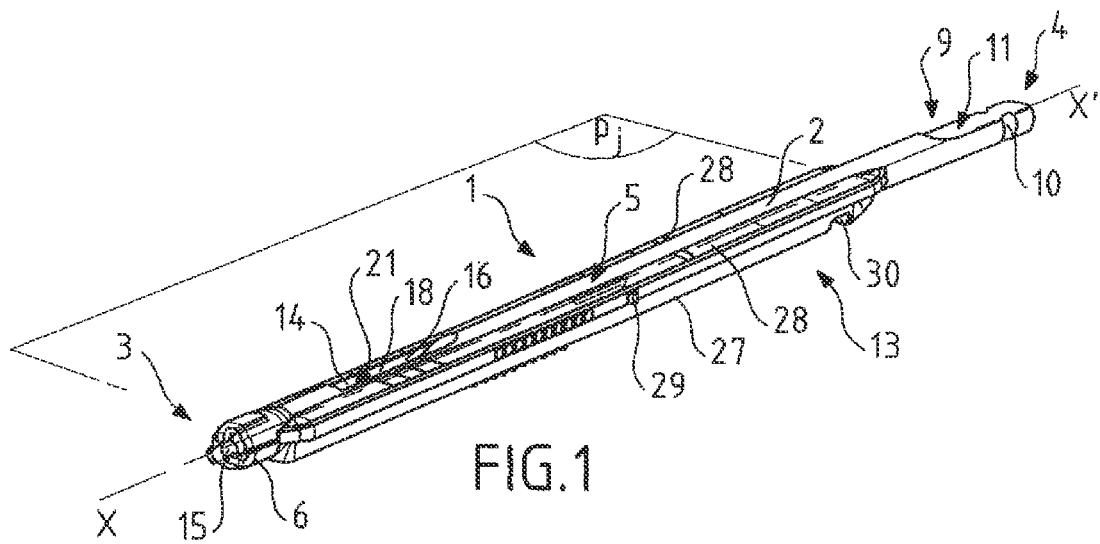
FIG. 1 is a general view in perspective showing a first variant of a surgical tool in accordance with the invention, comprising in particular an extension working endpiece designed specifically for putting surgical pins into place.
Figure 2:
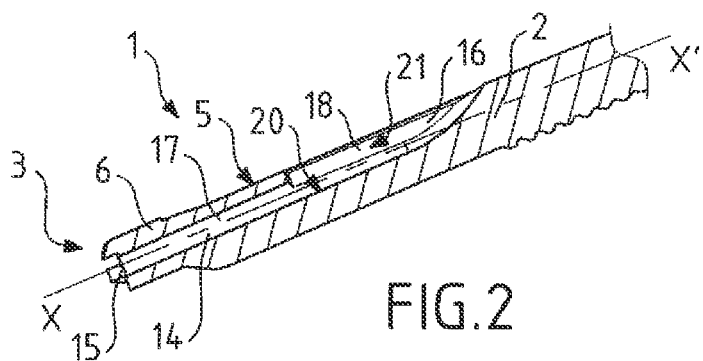
FIG. 2 is a side view in longitudinal section showing an embodiment detail of the first variant of the FIG. 1 surgical tool.
Figure 3:
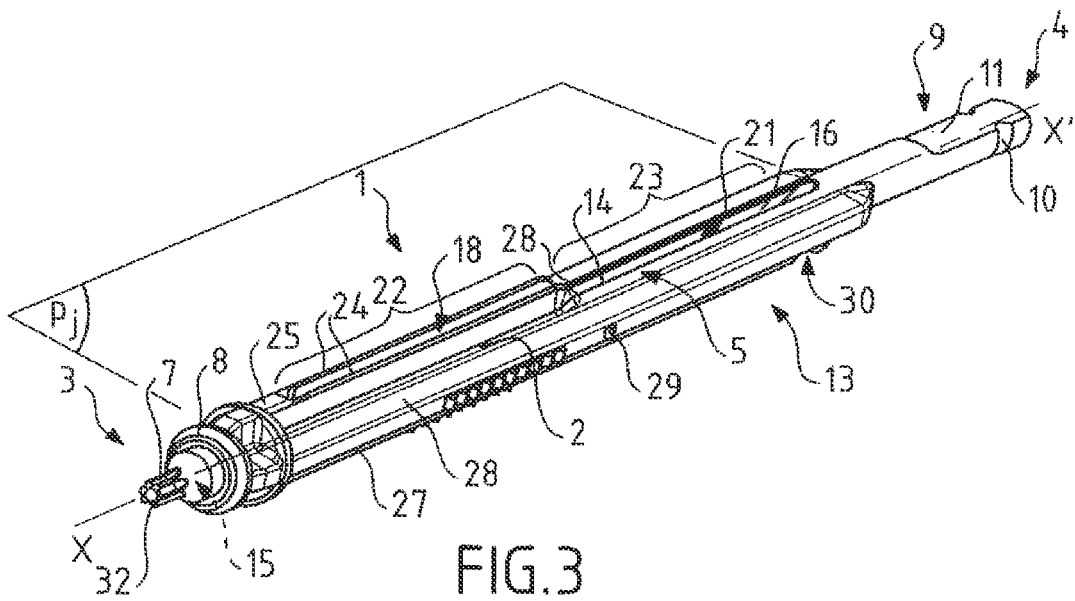
FIG. 3 is a general perspective view showing a second variant of a surgical tool in accordance with the invention, including in particular a fitted working endpiece designed specifically to enable an osteosynthesis screw to be tightened.

The invention provides a surgical tool 1 as such for inserting surgical implants in a patient's body. FIGS. 1 and 2 show a first embodiment of a surgical tool in accordance with the invention, while FIGS. 3 and 4 show a second embodiment of a surgical tool, likewise in accordance with the invention. In any event, the surgical tool 1 is designed to enable a surgeon to insert a surgical implant (not shown) in a patient's body, e.g. a screw, a clip, or a pin, e.g. during a surgical operation on said patient. Naturally, without going beyond the ambit of the invention, the surgical tool 1 could be used in the context of animal surgery, or for uses that do not involve surgery, e.g. for tightening a screw in a non-living mechanism.

The implants inserted using the surgical tool 1 are preferably osteosynthesis implants, i.e. for the purpose, by way of example, of repairing patient's bones after a fracture or a crack.

By way of example, the surgical tool 1 is hand-held, i.e. it can be moved directly by the surgeon's hand. Nevertheless, it is also possible to envisage fitting the surgical tool 1 to an appliance, in particular a rotary appliance, as described below. Furthermore, it is possible to combine the surgical tool 1 with other elements, such as for example a removable handle, as described below.

By way of example, the surgical tool 1 of the invention makes it possible to impart a turning force and/or axial force to the surgical implant, in particular when said implant is formed by an osteosynthesis screw, or indeed to impart a force that is exclusively axial.

In the invention, the surgical tool 1 has a main body 2 extending along a longitudinal axis X-X' between firstly a working end 3 and secondly a proximal end 4, the main body 2 also presenting an outside surface 5 connecting the working end 3 to the proximal end 4. The surgical tool 1 is advantageously constituted for the most part by the main body 2, which is preferably rigid, heavy, and solid over the majority of its volume, naturally with the exception of the functional openings, grooves, and orifices formed therein and as described below. The surgical tool 1 of the invention thus presents a general shape that is axially elongate between the working end 3 and the proximal end 4, extending along the longitudinal axis X-X'. Nevertheless, without going beyond the ambit of the invention, the surgical tool 1 could present a general shape that is curved, or T-shaped, or non-axial, providing at least a portion of the surgical tool situated between the working end 3 and the rear end 4 is substantially longitudinal. The surgical tool 1, and in particular its main body 2, is preferably made entirely out of a first material, e.g. a polymer material, so as to be capable of being made by molding, and of being sterilized, while also being robust and relatively inexpensive. Nevertheless, any other material that is rigid, moldable, sterilizable, and generally appropriate for the surgical environment could constitute the first material. A polymer presents the advantage of enabling the surgical tool to be fabricated in a manner that is so inexpensive that it may be disposable or for single use. Thus, the surgical tool 1 may be supplied in sterile form to the surgeon, thus avoiding any need for the surgeon to clean and sterilize the surgical tool prior to any surgical operation, and furthermore guaranteeing good sterility and cleanliness for the operating environment.

In the meaning of the invention, the outside surface 5 forms the external outline of the surgical tool 1 and of the main body 2, exclusively between the working end 3 and the proximal end 4. The outside surface 5 thus forms a lateral longitudinal surface of the surgical tool 1 and does not include the working end 3 or the proximal end 4.

The term "working end 3" is used to mean a distal end of the surgical tool that is to be made to turn beside the patient and, for example, to come into contact with a surgical implant for inserting into the patient's body. The working end 3 preferably presents an appropriate shape referred to as a "working endpiece" 6, 7 in order to engage with a given type of surgical implant, e.g. in order to work it and/or to put it into place in the patient's body.

For example, and as shown in FIGS. 1 and 2, the working endpiece 6 is made integrally with the main body 2 in order to form a working endpiece 6 extending the body at the working end 3. This extension working endpiece 6 thus preferably forms an integral one-piece item with the main body 2 so as to be very easy to fabricate, in particular at the same time as fabricating said main body 2. The extension working endpiece 6 is designed for example to put surgical pins into place.

Alternatively, and as shown by way of example in FIGS. 3 to 5, the surgical tool 1 preferably has a fitted working endpiece 7, i.e. that is secured to the main body 2 in order to form its working end 3. In this preferred alternative, the fitted working endpiece 7 and the main body 2 form distinct parts that are assembled together, for example. Preferably, the main body 2 has a reception portion 8 for receiving the fitted working endpiece 7, via which the fitted working endpiece 7 is secured to said main body 2. The reception portion 8 is made integrally with the main body 2, and it preferably forms a permanent connection with the fitted working endpiece 7 on said main body 2, e.g. such that it is advantageously necessary to break off said reception portion 8 in order to separate the fitted working endpiece 7 from said main body 2. In optional manner, the reception portion 8 presents the form of a body of revolution about the longitudinal axis X-X' and extends over a fraction of the main body 2 from its working end 3. Preferably, the surgical tool 1 is made entirely out of the above-described first material, e.g. a polymer material, with the exception of the fitted working endpiece 7 which is made out of a second material that is distinct from the first material, e.g. a metal material. Thus, the fitted working endpiece 7 is advantageously made of stainless steel or titanium, for example, so as to be particularly robust and hard, in particular when it forms a screwdriver endpiece, e.g. having a star shape (as shown in FIG. 5). The particularly great hardness of the fitted working endpiece 7 enables the surgical tool to be used with relatively high force in a surgical implant without requiring the tool to be made entirely out of the second material, which is generally more expensive and more difficult to work than the first material. The fitted working endpiece 7 is preferably incorporated with the main body 2 via the reception portion 8 during a step of molding the surgical tool 1 during fabrication, the fitted working endpiece 7 preferably being inserted in its final form in the mold that is to be used for molding the main body 2.

Opposite from the working end 3, the proximal end 4 constitutes the rear end of the surgical tool, e.g. for the purpose of pointing towards the surgeon who is using said surgical tool 1. By way of example, the surgical tool 1 is for being held in the surgeon's hand via the main body 2 and starting from the proximal end 4, with a specific grip zone then extending from the proximal end 4 along said main body 2. Preferably, the surgical tool 1 has connection means 9 for connecting said surgical tool 1 to a rotary appliance, e.g. a motor-driven appliance, such as a screwdriver or a drill, said connection means 9 being arranged in the vicinity of the proximal end 4. Advantageously, and as shown in the figures, the connection means 9 are formed by:

firstly an annular groove 10 enabling said surgical tool 1 to be held axially by the rotary appliance, said annular groove 10 being provided in the outside surface 5 of the main body 2 in the vicinity of the proximal end 4; and secondly a flat 11 for enabling said surgical tool 1 to be driven in rotation by the rotary appliance, e.g. by a motor thereof, said rotary drive flat 11 being arranged in the outside surface 5 of the main body 2.

Such a design advantageously enables the surgical tool 1 to be particularly versatile, and to be fitted to the rotary appliances that are most commonly used. The surgical tool 1 preferably has both a specific manual grip zone and the connection means 9.

Also advantageously, and as shown in FIG. 7, the surgical tool 1 includes a reception system 13 for receiving a handle 12 enabling said surgical tool 1 to be releasably assembled with said handle 12 so as to co-operate therewith to form a surgical instrument having a removable handle, by way of example, i.e. a surgical instrument that may be modular. The reception system 13, preferred variants of which are described in greater detail below, preferably forms a zone for receiving the removable handle 12. Preferably, the surgical tool 1 has both the reception system 13 and the connection means 9. The handle 12 preferably presents the shape of a conventional screwdriver handle, as shown in FIG. 7, but alternatively it could be in the form of a knob or a grip. The surgical tool 1 may thus advantageously form a removable surgical screwdriver endpiece (as shown for example in FIGS. 3 and 4), or a removable endpiece for inserting surgical pins (e.g. as shown in FIGS. 1 and 2), designed to have a handle 12 fitted thereon. Thus, and in advantageous manner, the same surgical tool 1 can be associated with a plurality of distinct handles 12, e.g. presenting different functions or shapes, with a given handle 12 being suitable for being associated with a plurality of surgical tools 1 of different functions or shapes, and for example provided with respective working endpieces 6 having different functions.

The surgical tool 1 of the invention also has a guide cannula 14 arranged within the main body 2 and extending between a distal orifice 15 opening to the outside of said main body 2 at the working end 3, and a rear orifice 16. The guide cannula 14 thus extends through the inside of the main body 2 over at least a fraction of its length, and preferably substantially along the longitudinal axis X-X', and it is advantageously designed to receive a guide rod, e.g. a metal wire, enabling the maneuvering of said surgical tool along said guide rod to be guided when the rod is engaged in and moves inside the guide cannula 14, sliding from the distal orifice 15.

The guide cannula preferably has only two access orifices, constituted by the distal orifice 15 and the rear orifice 16, which orifices are distinct and separate, and form a connection, preferably a single connection, between the outside of the surgical tool 1 and the inside of the guide cannula 14. The guide cannula 14 advantageously forms a rectilinear guide sheath over at least a majority of its length starting from the distal orifice 15 so as to receive within said guide sheath a rectilinear guide rod, which may for example be substantially rigid. Naturally, it is also possible for the guide cannula 14 to be non-rectilinear, and for example for it to be curved, folded, or undulating.

The shape of the guide cannula 14 nevertheless serves advantageously to allow the surgical tool to turn about the longitudinal axis X-X' when the guide rod is engaged in said guide cannula 14, the cannula being centered around the axis X-X' so as to contain the axis over the entire length of said guide cannula 14.

The distal orifice 15 is preferably circular in shape and is arranged specifically at the working end 3, advantageously in such a manner as to surround the longitudinal axis X-X'. The inside wall of the guide cannula 14 advantageously extends said distal orifice 15, which forms its starting point. The rear orifice 16 forms the other end of the guide cannula 14.

According to an important characteristic of the invention, the rear orifice 16 opens into the outside surface 5 of said main body 2. In other words, whereas the distal orifice 15 opens out at the working end 3 and preferably the majority at least of the guide cannula 14 extends along the longitudinal axis X-X' or parallel thereto, the rear orifice 16 is arranged in the outside surface 5 and not at the proximal end 4. The rear orifice 16 is thus arranged laterally on the surgical tool 1 like the lateral openings in a transverse flute, and not at one of its ends, in order to form a lateral window extending the guide cannula 14. The rear orifice 16 preferably forms an intermediate opening arranged in a middle portion of the main body 2, on an intermediate portion thereof situated between the proximal end 4 and the working end 3.

Such an arrangement is particularly advantageous insofar as the rear orifice 16 serves to extend the guide cannula 14 along the longitudinal axis X-X' over a length corresponding to the width of said rear orifice 16, i.e. to the size of the opening that it forms. It is thus possible, when fabricating the surgical tool 1, to create the guide cannula 14 in two portions:
- a first portion arranged in the main body 2, e.g. with the help of machining, going longitudinally from the distal orifice 15; and
- a second portion arranged in the main body 2, e.g. by machining, extending transversely from the rear orifice 16, so as to extend said first portion longitudinally.

The outline of the rear orifice 16 is preferably of a shape that is elongate in the longitudinal direction of the main body 2.

Nevertheless, without going beyond the ambit of the invention, the guide cannula 14 could be provided with a proximal orifice 33 opening out from the main body 2 at the proximal end 4, as shown by way of example in FIGS. 8 and 9. In this preferred configuration, the guide cannula 14 passes right through the main body 2 from one end to the other, and preferably presents a total of three orifices placed in this order along the longitudinal axis X-X': the distal orifice 15, the rear orifice 16, and the proximal orifice 33. In such an advantageous configuration, the surgical tool 1 is designed for example to receive a guide rod that is longer than the length of the main body 2 (from the working end 3 to the proximal end 4), said guide rod being capable of passing right through the surgical tool 1 via the guide cannula 14, e.g. entering via the distal orifice 15 and leaving via the proximal orifice 33.

As shown in the figures, and in particularly advantageous manner, the guide cannula 14 is formed by:
- a main tubular channel 17 extending over a first portion of the guide cannula 14 from the distal orifice 15 along the longitudinal axis X-X'; and
- an open channel 18 arranged in the outside surface 5 extending from the rear orifice 16 so as to extend the main tubular channel 17, the open channel 18 advantageously forms the rear orifice 16.

The main tubular channel 17 preferably forms an inside duct or an inside tunnel of the main body 2 and is preferably of generally cylindrical or frustoconical shape coaxial about or parallel with the longitudinal axis X-X' in order to receive the guide rod so as to surround it over its entire periphery. The open channel 18 preferably extends the main tubular channel 17 along the longitudinal axis X-X' so as to form a guide cannula 14 that is rectilinear along said longitudinal axis X-X'. The guide cannula 14 is preferably designed to receive a guide rod, specifically forming a guide wire, for guiding said surgical tool 1 over the entire length of said guide cannula 14, and specifically from the distal orifice 15 and then over the length of the main tubular channel 17, and finally over the entire length of the open channel 18.

Preferably, the main tubular channel 17 extends along the longitudinal axis X-X', the open channel 18 being formed by:
- a groove bottom 20 extending the main tubular channel 17 along the longitudinal axis X-X' over at least a fraction of the length of the surgical tool 1; and
- two channel walls 21 rising from the bottom to the outside surface 5.

Since the main tubular channel 17 is thus preferably formed by a tubular inside wall of the main body 2, the open channel 18 extends said inside wall over a fraction only of its circumference, preferably so as to form the groove bottom 20, i.e. the bottom of the open channel 18, said groove bottom 20 being in alignment with said inside wall.

In this configuration, the guide rod may be inserted in the guide cannula 14 so as to begin by moving within the tubular channel 17, and then between the walls of the channel 21 in the vicinity of the groove bottom 20, or in contact with said groove bottom 20. The open channel 18 thus preferably surrounds the guide rod over only a fraction of its circumference. Advantageously, the guide rod is thus visible from outside the surgical tool 1 when it is inserted in the open channel 18, whereas it is not visible while it is contained exclusively in the tubular channel 17.

The main tubular channel 17 thus advantageously makes it possible to hold the guide rod in all directions extending transversely to the longitudinal axis X-X' so that the guidance of the surgical tool 1 by said rod is very accurate, in spite of the presence of an open portion of the guide cannula 14 as formed by the open channel 18. Furthermore, the length of the open channel 18 along the longitudinal axis X-X' makes it possible in practice for the surgical tool to present a guide cannula 14 that is particularly long, and suitable for receiving guide rods that are long and rigid.

In the preferred embodiment shown in FIGS. 3 and 4, the fitted working endpiece 7 preferably includes an auxiliary tubular channel 19 arranged therein from a working orifice 32, so that the auxiliary tubular channel 19 extends the guide cannula 14 from the distal orifice 15 to the working orifice 32. The surgical tool 1 is thus advantageously designed so that the guide rod moves in the guide cannula 14 while also moving in the auxiliary tubular channel 19 inside the fitted working endpiece 7. When the fitted working endpiece 7 is a screwdriver endpiece, the screw for tightening preferably has a cannula so that it can likewise be guided by the guide rod by means of its own cannula in order to be tightened by the surgical tool 1 that is likewise guided by the same guide rod.

In the embodiment of FIGS. 1 and 2, the working orifice is preferably formed by and coincides with the distal orifice 15. In general manner, the surgical tool 1 is advantageously designed to implant implants having cannulas in a patient's body so that they can likewise be guided by the guide rod by means of their own cannulas, in order to be put into place in the patient's body by the surgical tool 1, which is itself guided by the same guide rod. This ensures that surgical implants can be put into place using the surgical tool 1 in a manner that is particularly accurate, easy, and reliable.

Given this particular design, the surgical tool 1 is particularly easy to fabricate. The surgical tool 1 is preferably designed to be made in a single molding operation, and for this purpose extends on either side of a join plane Pj carried by the longitudinal axis X-X' in such a manner that:
- the main body 2 and the open channel 18 taper relative to said join plane Pj; and
- the main tubular channel 17 tapers along the longitudinal axis X-X'.

The term "taper" is used to mean that the external outline of an object is provided with a slope that is sufficient to enable said object to be made by molding. For example, the walls of the channel 21 advantageously taper, for example being arranged symmetrically about a plane containing the longitudinal axis X-X' and being orthogonal to the join plane Pj, so as to diverge going away therefrom with a taper angle. The open channel 18 thus presents a V-shaped section.

The surgical tool 1 can thus be formed in a mold including a slide, in particular a mold having two mold cavities and at least a first slide. The main body 2 can thus advantageously be modelled by the two mold cavities on either side of the join plane Pj, the open channel 18 being created with the help of an appropriate negative shape in one of the two mold cavities. Since the main tubular channel 17 tapers along the longitudinal axis X-X', and since it is placed astride the join plane Pj, it can be formed with the help of the first slide, which is designed to be movable in translation along the longitudinal axis X-X'.

Advantageously, and as shown in FIGS. 3 and 4, the channel walls 21 extend from the main tubular channel 17:
over a splined portion 22 along which they are extended by two parallel longitudinal reinforcing fins 24 projecting from the outside surface 5 of the main body 2; and then
over a trough portion 23 along which the channel walls 21 open out from the outside surface 5 of the main body 2.

Thus, the open channel 18 preferably extends over a splined portion 22 along which it is particularly deep, the channel walls 21 specifically being particularly tall since they are extended by the longitudinal reinforcing fins 24, followed by a trough portion 23 along which said open channel 18 is shallower. Preferably, the longitudinal reinforcing fins 24 serve to stiffen the surgical tool 1, in particular in bending and in twisting, so that it can be made for the most part out of polymer, e.g. out of polyetheretherketone (PEEK), while being particularly robust and rigid.

Advantageously, and as shown in FIGS. 3 and 4, the surgical tool 1 includes a front longitudinal spline 25 projecting from the main body 2 in a plane radial to the longitudinal axis X-X' so as to extend and unite the two longitudinal reinforcing fins 24 towards the working end 3. The front longitudinal spline 25 preferably extends in a plane that is radial relative to the longitudinal axis X-X' and orthogonal relative to the join plane Pj, thereby interconnecting the longitudinal reinforcing fins 24 and the reception portion 8. The front longitudinal spline 25 preferably extends over the entire length of the main tubular channel 17. The presence of a front longitudinal spline 25 serves advantageously to further reinforce the surgical tool 1 so that it is particularly robust and rigid, and also to reinforce the longitudinal reinforcing fins 24.

In the preferred configuration in which the guide cannula 14 has a proximal orifice 33, as shown by way of example in FIGS. 8 and 9, said guide cannula 14 may be formed, for example, by:
the above-described main tubular channel 17;
the above-described open channel 18; and in particular
a proximal tubular channel 34 extending from the open channel 18, e.g. from the trough portion 23, to the proximal orifice 33, so as to extend the open channel 18, and so that the guide cannula 14 passes through the main body 2 from the working end 3 to the proximal end 4.

The proximal tubular channel 34 preferably forms an inside duct or an inside tunnel in the main body 2, and is preferably of generally cylindrical or frustoconical shape coaxial with or parallel to the longitudinal axis X-X', so as to receive the guide rod in such a manner as to surround it over its entire periphery. The open channel 18 preferably extends the proximal tubular channel 34 along the longitudinal axis X-X' so as to form a rectilinear guide cannula 14 along said longitudinal axis X-X'. The guide cannula 14 is preferably designed to receive the guide rod starting from the distal orifice 15, and then along the entire length of the main tubular channel 17, over the entire length of the open channel 18, and finally over the entire length of the proximal tubular channel 34.

The guide cannula 14 thus serves to receive a guide rod, e.g. a rectilinear rod, that is engaged all along said guide cannula 14 so as to pass right through the surgical tool 1, being inserted via the distal orifice 15 and leaving via the proximal orifice 33.

The proximal tubular channel 34 is preferably tapered along the longitudinal axis X-X', symmetrically relative to the main tubular channel 17.

In a preferred variant of the invention in which the surgical tool 1 has a reception system 13 for receiving a removable handle 12, the handle advantageously includes a reception orifice 26 designed to receive the surgical tool 1 by means of the reception system 13, the reception system being designed to prevent said handle 12 from moving in rotation relative to said surgical tool 1 about the longitudinal axis X-X', while allowing said handle 12 to slide relative to said surgical tool 1 along the longitudinal axis X-X'. The surgical tool 1 can thus be inserted in the reception orifice 26 by sliding said surgical tool within said reception orifice 26 and in particular along the reception system 13. Complementary shapes for the reception orifice 26 and the reception system 13 advantageously enable the surgeon to turn the surgical tool 1 with the help of the removable handle 12 when they are assembled together.

Preferably, the reception system 13 comprises at least one main longitudinal spline 27 projecting from the main body 2 in a plane extending radially relative to the longitudinal axis X-X', the main longitudinal spline 27 being designed to co-operate with a main longitudinal slot of the reception orifice 26 of the handle 12 in order to constrain said handle 12 to move in rotation about the longitudinal axis X-X' together with said surgical tool 1. The main longitudinal spline 27 is preferably arranged symmetrically to the front longitudinal spline 25 about the join plane Pj.

The reception system 13 preferably also includes two auxiliary longitudinal splines 28 arranged symmetrically relative to the plane in which the longitudinal slot extends, and thus projecting from the main body 2 radially relative to the longitudinal axis X-X', each of the auxiliary longitudinal splines 28 being designed to co-operate with an auxiliary longitudinal slot of the reception opening of the handle 12 to move in order to contribute at least to constraining the handle 12 in rotation about the longitudinal axis X-X' together with said surgical tool 1. The presence of auxiliary longitudinal splines 28 serve to strengthen the congruent shapes of the reception system 13 and the reception orifice 26, thereby enabling the surgical tool 1 to slide freely in the reception orifice 26 while limiting slack in rotation about the longitudinal axis X-X'.

According to an important characteristic of the invention, the surgical tool 1, which is characterized in that its rear orifice 16 opens out into the outside surface 5 of the main body 2, is thus also characterized in that said main body 2 presents longitudinal splines 25, 27, 28 projecting from said main body 2 in planes extending radially relative to the longitudinal axis X-X'.

This serves to stiffen the surgical tool 1, making it possible to compensate for any zones of weakness that might result from the particular local shape of said main body 2.

Said longitudinal splines 25, 27, 28 preferably form reinforcing length members serving to stiffen the surgical tool in particular in bending and in twisting while also being arranged in such a manner that the surgical tool 1 can be made by molding, i.e. tapering relative to the join plane Pj. The main body 2 of the surgical tool 1 preferably has three longitudinal splines 27, 28 arranged in a T-shape (as shown for example in FIG. 1), or four longitudinal splines 25, 27, 28 arranged in a cross configuration (as shown for example in FIG. 3). The longitudinal slots of the reception orifice 26 are advantageously arranged in such a manner that it also preferably presents a section that is T-shaped or cross-shaped. Naturally, other shapes are possible without going beyond the ambit of the invention, and in particular shapes that are not bodies of revolution about the longitudinal axis X-X' so as to enable the handle 12 to turn the surgical tool 1 about said longitudinal axis X-X'.

Furthermore, the surgical tool 1 advantageously includes at least one stop lug 29 for stopping movement in translation along the longitudinal axis X-X' of the handle 12, the stop lug 29 being designed to form an end stop for movement in translation of the handle 12 towards the working end 3 of the surgical tool 1. The stop lug 29 is preferably formed by one or more spikes or bulges projecting from the outside surface 5, in particular beside at least one of the longitudinal splines, e.g. the auxiliary longitudinal splines 28. Because of the presence of the stop lug 29, it is possible to apply axial thrust on the surgical tool 1 towards the working end 3 along the longitudinal axis X-X' by means of the handle 12.

Advantageously, the surgical tool 1 has a blocking element 30, e.g. formed by a blocking lug or a blocking notch, that is arranged at the outside surface 5 of the main body 2, and in particular of the main longitudinal spline 27, or of another one of the longitudinal splines 25, 27, 28.

The handle 12 is advantageously provided with actuatable blocking means 31, e.g. a blocking lever, designed to move between:

firstly a blocking configuration in which the blocking means 31 block sliding of the handle along the longitudinal axis of the surgical tool 1 by co-operating shapes with the blocking element 30; and secondly a release configuration in which the blocking means 31 allow the handle to slide along the longitudinal axis of the surgical tool 1.

Consequently, the blocking means 31 advantageously enables the surgical tool 1 to be secured, preferably completely, to the handle 12.

The blocking means 31 are preferably formed by a blocking lever, which lever has a blocking catch designed to be inserted or to insert itself in the blocking element 30 formed by a blocking notch (as shown in the figures). The sliding of the surgical tool 1 along the longitudinal axis X-X' is then advantageously blocked when the blocking lever is in the blocking configuration.

The invention also provides as such a surgical kit comprising at least one surgical tool 1 as described above together with a removable handle 12, e.g. as described above, and preferably at least two surgical tools 1 as described above for performing different functions.

The term "different functions" is used to mean that the two surgical tools that can be formed with the respective handles 12 may be a first surgical instrument with a removable handle, and a second surgical instrument with a removable handle and having a function that is different from the function of said first surgical instrument with a removable handle, i.e. said surgical instruments are for performing actions that are distinct and not similar, for putting into place or removing surgical implants that are different in terms of size or function, or indeed for interacting differently with the operating environment and with the patient's body. For example, surgical tools of different functions may be used for tightening or loosening a first screw having a first shape of head socket, and a second screw having a second shape of head socket different from the first head socket. For example, the surgical kit comprises a surgical tool 1 in accordance with the variant shown in FIGS. 1 and 2 and another surgical tool 1 in accordance with the variant shown in FIGS. 3 and 4.

The surgical kit 1 may advantageously constitute a kit that is for single use or disposable.

The surgical tool kit preferably also advantageously includes wires, pins, screws, clips, and additional surgical instruments enabling the surgeon to perform a predetermined type of surgical operation.

The invention also provides as such a method of fabricating a surgical tool 1 as described above, said method comprising a single molding step during which said surgical tool 1 is made in full.

In other words, the fabrication method of the invention enables the surgical tool 1 as described above to be made in a single operation, without any other finishing operation such as machining or the like. The material for molding during the fabrication method is advantageously a polymer. When the surgical tool 1 advantageously includes a fitted working endpiece 7, the surgical tool is preferably made and assembled therewith during a single molding operation.

Preferably, the fabrication of the surgical tool takes place as follows:

fabricating or optionally supplying a fitted working endpiece 7;

placing said fitted working endpiece 7 in a mold of a fabrication machine for fabricating the surgical tool 1, e.g. a mold having slides, the fabrication machine including for example a tapered cylindrical slide enabling the main tubular channel 17 to be formed, with said fitted working endpiece 7 being engaged via its auxiliary tubular channel 19 on said slide;

pouring or casting or injecting the material that is to form the surgical tool 1 into the mold of the machine in such a manner that the material is modelled by said mold around the slide and around the fitted working endpiece 7; and withdrawing the slide and then opening the mold once the material has been modelled, the material then forming the surgical tool 1 secured to the fitted working endpiece 7 and in its final shape.

Finally, the invention provides as such a fabrication machine (not shown) for fabricating a surgical tool 1 as described above, enabling the above-described fabrication method to be performed.

Preferably, the fabrication machine of the invention comprises a mold having a first mold cavity, a second mold cavity, and at least a first slide, designed together to form a closed space in which a material for forming the surgical tool is to be cast. Preferably, when the material is cast into the mold:

the first mold cavity and the second mold cavity are designed together to model the material so as to form the main body 2 and the rear orifice 16, in particular the open channel 18, around the join plane Pj; and the first slide being designed to provide the working orifice 3 within the main body 2 and in particular the main tubular channel 17.

The fabrication machine of the invention thus advantageously forms a mold with slides.

In the meaning of the invention, "modeling" means imparting a shape to the material by molding.

The first cavity is advantageously designed to model the portion of the surgical tool 1 extending from the join plane Pj in a first direction, the second cavity being designed to model the portion of the surgical tool 1 extending from the join plane Pj in a second direction opposite to the first direction.

When the mold is closed, i.e. when the first cavity is brought up against the second cavity, the slide is preferably designed to extend along the join plane Pj so as to form the working orifice 3 and in particular the main tubular channel 17. The slide is preferably designed to receive the fitted working endpiece 7, which is itself designed to be engaged on said slide via the auxiliary tubular channel 19.

Optionally, the fabrication machine could include a second slide similar to the first slide for the purpose of making the proximal tubular channel 34 and the proximal orifice 33, the second slide being designed for example to be movable along the longitudinal axis X-X'.

The fabrication machine of the invention thus makes it possible to make the surgical tool in a manner that is particularly easy, rapid, and inexpensive.

The invention claimed is:

1. A surgical tool (1) for inserting surgical implants in a patient's body, the tool comprising:
    a main body (2) extending along a longitudinal axis (X-X') between firstly a working end (3) and secondly a proximal end (4), the main body (2) also presenting an outside surface (5) connecting the working end (3) to the proximal end (4); and
    a guide cannula (14) arranged within the main body (2) and extending between a distal orifice (15) opening to the outside of said main body (2) at the working end (3), and a rear orifice (16) disposed intermediate said working end and said proximal end;
    said surgical tool (1) being characterized in that said rear orifice (16) opens out to the outside surface (5) of said main body (2), and in that said main body (2) presents longitudinal splines (25, 27, 28) projecting from said main body (2) in respective planes extending radially relative to the longitudinal axis (X-X').

2. A surgical tool (1) as defined in claim 1 in which said guide cannula (14) is formed by:
    a main tubular channel (17) extending over a first portion of the guide cannula (14) from the distal orifice (15) along the longitudinal axis (X-X'); and
    an open channel (18) arranged in the outside surface (5) extending from the rear orifice (16) so as to extend the main tubular channel (17).

3. A surgical tool (1) as defined in claim 2 in which said tool is designed to be made in a single molding operation, and for this purpose extends on either side of a join plane (Pj) carried by the longitudinal axis (X-X') in such a manner that:
    the main body (2) and the open channel (18) taper relative to said join plane (Pj); and
    the main tubular channel (17) tapers along the longitudinal axis (X-X').

4. A surgical tool (1) as defined in claim 2 in which the open channel (18) is formed by:
    a groove bottom (20) extending the main tubular channel (17) along the longitudinal axis (X-X') over at least a fraction of a length of the surgical tool (1); and
    two channel walls (21) rising from the bottom to the outside surface (5).

5. A surgical tool (1) as defined in claim 4 in which the channel walls (21) extend from the main tubular channel (17):

over a splined portion (22) along which they are extended by two parallel longitudinal reinforcing fins (24) projecting from the outside surface (5) of the main body (2); and then
over a trough portion (23) along which the channel walls (21) open out from the outside surface (5) of the main body (2).

6. A surgical tool (1) as defined in claim 5 in which said tool includes a front longitudinal spline (25) projecting from the main body (2) in a plane radial to the longitudinal axis (X-X') so as to extend and unite the two longitudinal reinforcing fins (24) towards the working end (3).

7. A surgical tool (1) as defined in claim 1 in which said tool includes a fitted working endpiece (7) secured to the main body (2) to form its working end (3), the fitted working endpiece (7) including an auxiliary tubular channel (19) arranged therein from a working orifice (32), so that the auxiliary tubular channel (19) extends the guide cannula (14) from the distal orifice (15) to the working orifice (32).

8. A surgical tool (1) as defined in claim 7 in which the main body (2) has a reception portion (8) for receiving the fitted working endpiece (7), via which the fitted working endpiece (7) is secured to said main body (2), the reception portion (8) being generally in the form of a body of revolution about the longitudinal axis (X-X') and extending over a fraction of the main body (2) from its working end (3).

9. A surgical tool (1) as defined in claim 8 in which the surgical tool (1) is made entirely out of a first material, with the exception of the fitted working endpiece (7) which is made out of a second material that is distinct from the first material.

10. A surgical tool (1) as defined in claim 1 in which said tool includes a connector (9) for connecting said surgical tool (1) to a rotary appliance, said connector (9) being arranged in a vicinity of the proximal end (4).

11. A surgical tool (1) as defined in claim 1 in which said tool includes a receptor (13) for receiving a handle (12) enabling said surgical tool (1) to be releasably assembled with said handle (12) so as to co-operate therewith to form a surgical instrument having a removable handle.

12. A surgical tool (1) as defined in claim 11 in which the handle (12) includes a reception orifice (26) designed to receive the surgical tool (1) by means of the receptor (13), the receptor being designed to prevent said handle (12) from moving in rotation relative to said surgical tool (1) about the longitudinal axis (X-X'), while allowing said handle (12) to slide relative to said surgical tool (1) along the longitudinal axis (X-X').

13. A surgical tool (1) as defined in claim 12 in which the receptor (13) comprises at least one main longitudinal spline (27) projecting from the main body (2) in a plane extending radially relative to the longitudinal axis (X-X'), the main longitudinal spline (27) being designed to co-operate with a main longitudinal slot of the reception orifice (26) of the handle (12) to move in order to constrain said handle (12) in rotation about the longitudinal axis (X-X') together with said surgical tool (1).

14. A surgical tool (1) as defined in claim 13 in which the receptor (13) also includes two auxiliary longitudinal splines (28) arranged symmetrically relative to the plane in which the longitudinal slot extends, radial relative to the longitudinal axis (X-X'), each of the auxiliary longitudinal splines (28) being designed to co-operate with an auxiliary longitudinal slot of the reception opening of the handle (12) in order to contribute at least to constraining the handle (12) to move in rotation about the longitudinal axis (X-X') together with said surgical tool (1).

15. A surgical tool (1) as defined in claim 11 in which said tool includes at least one stop lug (29) for stopping movement in translation along the longitudinal axis (X-X') of the handle (12), the stop lug (29) being designed to form an end stop for movement in translation of the handle (12) towards the working end (3) of the surgical tool (1).

16. A surgical tool (1) as defined in claim 11 in which said tool includes a blocking element (30), arranged at the outside surface (5) of the main body (2), the handle (12) being provided with an-actuatable blocker (31) designed to move between:
    firstly a blocking configuration in which the blocker (31) blocks sliding of the handle along the longitudinal axis of the surgical tool (1) by co-operating shapes with the blocking element (30); and
    secondly a release configuration in which the blocker (31) allows the handle to slide along the longitudinal axis of the surgical tool (1).

17. A surgical tool (1) as defined in claim 11 in which said tool includes a removable endpiece of a surgical screwdriver or a removable endpiece for inserting surgical pins.

18. A surgical tool (1) according to claim 1 in which said guide cannula (14) is provided with a proximal orifice (33) opening out from the main body (2) at the proximal end (4).

19. A surgical tool as defined in claim 1 comprising a surgical kit having at least one surgical tool (1) and a removable handle (12).

20. A surgical tool (1) as defined in claim 1 being produced according to a method, the method being characterized in that it comprises a single molding step during which said surgical tool (1) is made in full.

21. A surgical tool (1) as defined in claim 1 being produced by a fabrication machine, the fabrication machine of the invention comprising a mold having a first mold cavity, a second mold cavity, and at least a first slide, designed together to form a closed space in which a material for forming the surgical tool is to be cast:
    the first mold cavity and the second mold cavity being designed together to model the material so as to form the main body (2) and the rear orifice (16), at least in part; and
    the first slide being designed to provide the working orifice (3) within the main body (2).

* * * * *